(12) United States Patent
Mermel et al.

(10) Patent No.: US 11,723,997 B2
(45) Date of Patent: Aug. 15, 2023

(54) UV LIGHT DISINFECTION AND CLEANING OF NARROW TUBE LUMENS

(71) Applicant: Bak & Mermel LLC, Barrington, RI (US)

(72) Inventors: Leonard A. Mermel, Barrington, RI (US); Jimmy Bak, Greve (DK)

(73) Assignee: Bak & Mermel LLC, Barrington, RI (US)

( * ) Notice: Subject to any disclaimer, the term of this patent is extended or adjusted under 35 U.S.C. 154(b) by 18 days.

(21) Appl. No.: 17/575,254

(22) Filed: Jan. 13, 2022

(65) Prior Publication Data

US 2022/0175990 A1 Jun. 9, 2022

Related U.S. Application Data

(63) Continuation of application No. 17/262,130, filed as application No. PCT/US2019/043495 on Jul. 25, 2019, now Pat. No. 11,246,953.
(Continued)

(51) Int. Cl.
*A61L 2/10* (2006.01)
*A61B 90/70* (2016.01)
(Continued)

(52) U.S. Cl.
CPC ............... *A61L 2/10* (2013.01); *A61B 1/121* (2013.01); *A61B 90/70* (2016.02); *A61L 2/26* (2013.01);
(Continued)

(58) Field of Classification Search
CPC ... A61L 2/10; A61L 2/26; A61B 90/70; A61B 2090/701; B08B 7/0057; B08B 2209/032; G02B 2006/0325; A61M 2025/0019
See application file for complete search history.

(56) References Cited

U.S. PATENT DOCUMENTS 7,175,806 B2 2/2007 Deal et al.
7,634,996 B2 12/2009 Gaska et al.
(Continued)

FOREIGN PATENT DOCUMENTS

EP 1197177 A2 4/2002
EP 2744522 A1 6/2014
KR 101784213 B1 10/2017

OTHER PUBLICATIONS

Extended European Search Report dated Feb. 25, 2022 in European Patent Application No. 19839979.2, 5 pages.
(Continued)

*Primary Examiner* — Natasha N Campbell
(74) *Attorney, Agent, or Firm* — Perkins Coie LLP

(57) ABSTRACT

Systems and methods for cleaning and disinfecting contaminated tube lumens are described herein. One system includes an ultraviolet light source and a sterile fluid reservoir fluidly coupled to a liquid light guide. The system is configured to allow simultaneous access and propagation of ultraviolet light and fluid in a tube having a lumen to be cleaned and disinfected. The light guide can be moved inside the tube and simultaneously emit ultraviolet light through its walls and at its distal end into the interior of the contaminated tube. A flush of sterile fluid from an open end of the liquid light guide removes debris and micro-organism detached from the inner surface during light exposure. The sterile fluid can be a high refractive index ionic solution promoting light propagation.

17 Claims, 10 Drawing Sheets

Related U.S. Application Data

(60) Provisional application No. 62/703,786, filed on Jul. 26, 2018.

(51) Int. Cl.
  *A61B 1/12* (2006.01)
  *A61L 2/26* (2006.01)
  *A61M 25/00* (2006.01)
  *B08B 7/00* (2006.01)
  *B08B 7/04* (2006.01)
  *B08B 9/032* (2006.01)
  *G02B 6/032* (2006.01)

(52) U.S. Cl.
  CPC .......... *A61M 25/00* (2013.01); *B08B 7/0057* (2013.01); *B08B 7/04* (2013.01); *B08B 9/032* (2013.01); *G02B 6/032* (2013.01); *A61B 2090/701* (2016.02); *A61L 2202/11* (2013.01); *A61L 2202/17* (2013.01); *A61L 2202/24* (2013.01); *A61M 2025/0019* (2013.01); *B08B 2209/032* (2013.01); *G02B 2006/0325* (2013.01)

(56) References Cited

U.S. PATENT DOCUMENTS

| | | |
|---|---|---|
| 8,556,950 B2 | 10/2013 | Rioux et al. |
| 9,205,162 B2 | 12/2015 | Deal et al. |
| 9,555,143 B2 | 1/2017 | Deal et al. |
| 10,279,058 B2 | 5/2019 | Lin et al. |
| 2003/0018373 A1 | 1/2003 | Eckhardt et al. |
| 2008/0051736 A1 | 2/2008 | Rioux et al. |
| 2012/0321509 A1 | 12/2012 | Bak |
| 2017/0119915 A1 | 5/2017 | Lin et al. |
| 2017/0182194 A1 | 6/2017 | Shin et al. |
| 2019/0008607 A1 | 1/2019 | Bauco et al. |
| 2019/0038789 A1 | 2/2019 | Kang et al. |
| 2021/0244840 A1 | 8/2021 | Mermel |

OTHER PUBLICATIONS

Blatchley III, et al., "Disinfection by Ultraviolet Irradiation." Disinfection, sterilization, and preservation, 2001, Chapter 41, pp. 823-852.

International Search Report and Written Opinion dated Nov. 8, 2019 in International Patent Application No. PCT/US19/43495, 12 pages.

Non-Final Office Action dated Jul. 8, 2021 in U.S. Appl. No. 17/262,130, 10 pages.

Notice of Allowance dated Oct. 29, 2021 in U.S. Appl. No. 17/262,130, 7 pages.

Ofstead, C. et al., "Longitudinal assessment of reprocessing effectiveness for colonoscopes and gastroscopes: Results of visual inspections, biochemical markers, and microbial cultures." American Journal of Infection Control, vol. 45 (2017), pp. e26-e33.

Rutala, W.A. et al., "Disinfection and sterilization: An overview." American Journal of Infection Control, vol. 41 (2013), pp. S2-S5.

Rutala, W.A. et al., "Gastrointestinal Endoscopes. A Need to Shift From Disinfection to Sterilization?" American Medical Association, Oct. 8, 2014, vol. 312, No. 14, 2 pages.

UV LIGHT DISINFECTION AND CLEANING OF NARROW TUBE LUMENS

CROSS-REFERENCE TO RELATED APPLICATIONS

This application is a continuation of U.S. patent application Ser. No. 17/262,130, titled "UV LIGHT DISINFECTION AND CLEANING OF NARROW TUBE LUMENS," filed Jan. 21, 2021, which is a National Phase of International Patent Application No. PCT/US 19/43495, titled "UV LIGHT DISINFECTION AND CLEANING OF NARROW TUBE LUMENS" filed Jul. 25, 2019, which claims priority to U.S. Provisional Patent Application No. 62/703,786, titled "UV LIGHT DISINFECTION AND CLEANING OF NARROW TUBE LUMENS," filed Jul. 26, 2018, the disclosures of which are hereby incorporated by reference in their entireties.

TECHNICAL FIELD

The present technology is related to systems and methods for cleaning and disinfecting contaminated tube lumens. In particular, various embodiments of the present technology are related to systems and methods for cleaning and disinfecting endoscope channels via ultraviolet light exposure.

BACKGROUND

The cleaning and high-level disinfection of reusable medical instruments, such as endoscopes, is guided by regulations and techniques provided by manufacturers and disinfection efficiency is assessed by microbiologically validated methods. However, scientific reports document that contamination with organic debris and residues of the inner lumen of tubes and mechanical parts, such as valves, remain even after an extensive cleaning and disinfection with potent chemicals. It is also known from other medical tubing, such as urinary and venous catheters, that residues on inner tube surfaces may harbor microorganisms.

In a review of chemical sterilants used for disinfection and sterilization of medical devices by Rutala and Weber (2013), the authors point out that one major drawback with the use of liquid chemical sterilants is that medical devices treated with a sterilant cannot be wrapped into the sterilant and maintained in contact with the sterilant during storage. Endoscopes must be dried during storage before they are used again. As such, the used liquid sterilant has to be applied for a preset time, then removed, and the endoscope channels have to be flushed and emptied for sterilant residues before drying and storage.

Concerns about achieved log reductions of high-level disinfection of gastrointestinal endoscopes by current sterilants have been addressed by Rutala and Weber (2014). Based on clinical observations the contamination level of potential pathogenic microorganisms in endoscopes is found to be in the range $10^{8-10}$. The initial cleaning step results in a 4-6 log reduction and the following high-level disinfection step with chemical sterilants in another 4-6 log reduction. In total, between 8-12 log reductions can be achieved leaving an unsafe margin of 0-2 log reductions.

A study by Ofstead and co-workers (2017), based on visual inspection with a borescope of endoscope channels, verified that the inner channel surfaces were contaminated even after repeated reprocessing following current guidelines. The same study demonstrated that microbial growth was observed in 60% of the endoscopes. Several reports support the finding that biofilm formation in the channels is present even after repeated cleaning following current guidelines. Ofstead and colleagues also reported that up to 95% of endoscopes cleaned and disinfected—and then claimed patient-ready—contained fluid residues. The residual fluid characteristics varied from clear, cloudy, opaque, or shimmery. Endoscopy-associated outbreaks have also been observed when current guidelines for endoscope reprocessing have been followed. Based on available data in the published literature, additional methods for cleaning and disinfection that can reduce the microbial contamination are needed.

DETAILED DESCRIPTION

Figure 1:
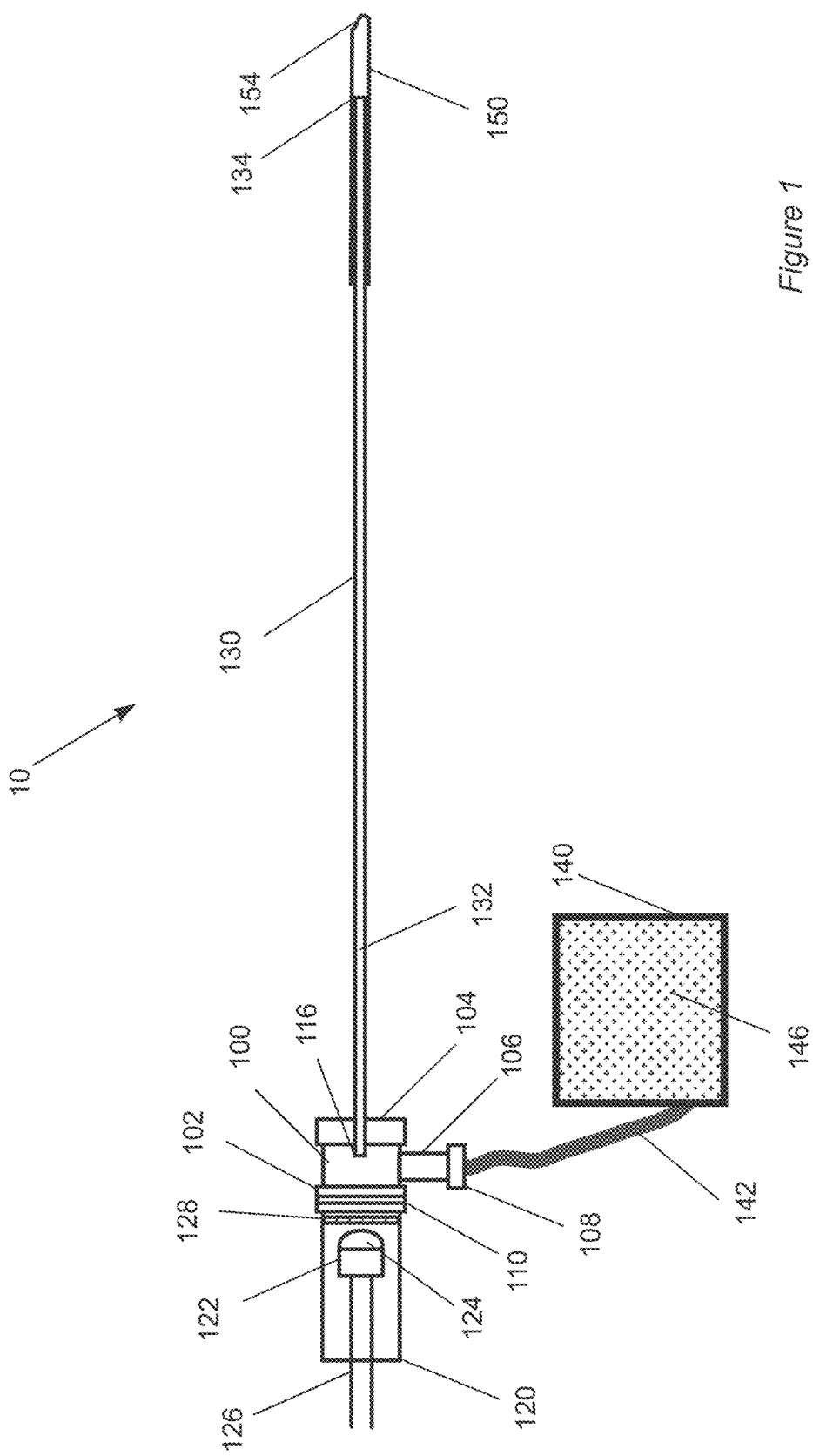
FIG. 1 is a partially schematic view of a system or assembly for cleaning and disinfecting medical tubing configured in accordance with an embodiment of the present technology.

Systems and methods in accordance with embodiments of the present technology are directed to disinfecting a lumen of a medical device (e.g., an endoscope) using ultraviolet (UV) light. For example, a method for disinfecting a medical device can include positioning at least a portion of an elongated tube of a liquid light guide within a lumen of the medical device, and flowing a fluid into the elongated tube such that the fluid flows (a) at least partially through a lumen of the elongated tube and (b) from a distal opening of the elongated tube and into the lumen of the medical device. The fluid (e.g., a saline solution) can have a refractive index that is greater than a refractive index of the elongated tube to facilitate UV light propagation there through. The method can further include, while following the fluid path, directing UV light into the elongated tube such that the UV light propagates (a) distally along the lumen of the elongated tube and (b) from the distal opening into the lumen of the medical device. Accordingly, embodiments of the present technology can advantageously enable simultaneous flushing and UV light disinfection of the medical device.

Specific details of several embodiments of the present technology are described herein with reference to FIGS. 1-10. Although many of the embodiments are described with respect to devices, systems, and methods for disinfecting medical devices such as endoscopes, other applications and other embodiments in addition to those described herein are within the scope of the present technology. For example, at least some embodiments of the present technology may be useful for disinfecting other types of devices having channels or lumens. It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

As used herein, the terms "distal" and "proximal" define a position or direction with respect to a light source and/or fluid source. The terms, "distal" and "distally" refer to a position distant from or in a direction away from a light source and/or fluid reservoir along the length of device. The terms "proximal" and "proximally" refer to a position near or in a direction toward a light source and/or fluid reservoir along the length of device. The headings provided herein are for convenience only and should not be construed as limiting the subject matter disclosed.

I. OVERVIEW

As set forth above, current methods for disinfecting gastrointestinal endoscopes using sterilants can result in an unsafe reduction in contamination. Ultraviolet technology is a promising technology because its disinfection efficiency is proportional to both the applied exposure time with an approximate one log reduction when the exposure time is doubled and the applied UV power is constant. In addition, the ongoing development of much more powerful UV light emitting sources (LEDs) sources will enhance the disinfection efficiency substantially for a pre-set time of UV treatment. In common clinical practice, an endoscope is first manually cleaned, then placed in an automated endoscope washer followed by an ethanol flush before storage under dry conditions in a safety cabinet. With the use of UV light distributed with a liquid light guide in the channel lumen of the endoscope, there can be three options for further enhancing the disinfection level of the endoscope channel. First, the UV disinfection procedure can be used immediately after removal from the automated washer. At this step, debris can be removed by the ionic flush simultaneously with UV exposure of the endoscope channel. The ionic solution can be removed from the endoscope channel with an ethanol flush and the endoscope can then then stored under dry conditions. Alternatively, the endoscope can be reprocessed as above, followed by use of the UV technology with a closed liquid light guide placed in the endoscope channel during storage in the safety cabinet. In this configuration, the endoscope channel undergoes continuous disinfection as long as the UV light source is powered. For this latter use, both the UV light source and the connector interfacing to the light guide can be inside the storage cabinet. Lastly, the endoscope is first cleaned manually and then placed in an automated endoscope washer followed by an ethanol flush as per usual reprocessing protocol. Then, the UV technology with a closed liquid light guide can be placed in the endoscope channel during storage in the safety cabinet.

UV light can be used for disinfection and is used in several clinical applications. The most effective UV light for disinfection is in the wavelength range 220-290 nm (UVC light). UVC light is, however, easily absorbed by chemical compounds. Consequently, fluid residues and surface contamination with biological or organic agents present in patient-ready endoscopes reduce the disinfection efficiency of UVC light-based technologies. In addition, fluids which appear cloudy and opaque scatter light and reduce light transmittance dramatically which further reduces disinfection efficiency. Therefore, to obtain an efficient and safe use of UVC light, a method for cleaning of the inner surfaces and removal of debris that attenuates light is important.

Another important requirement for a disinfection technology based on physical methods (e.g., as an alternative to conventional chemical-based methods) is that the equipment in contact with a used medical device be low cost and disposable in order to avoid potential cross-contamination between uses.

UVC disinfection of the inner surfaces of endoscope channels using a fused silica fiber inserted into tube lumen has been proposed as a solution. Insertion of a mechanical device like an optical fiber in very narrow operating channels (2-4 mm) results in contact of the mechanical device with the channel wall or residual fluid. Contamination of the small area optical fiber tip or diffuser that emits the UV light is a serious problem because disinfection efficiency is reduced to an unknown level. In addition, the physical contact between the fiber probe and channel wall also allow debris to be detached from the surface and remain in the channel after disinfection. Another technical problem is that optical fiber materials that are transparent for UVC light (e.g., UV grade quartz) can be very fragile and break easily. Besides the aforementioned technical problems, the high costs of the fused silica fibers make them less obvious as a first choice as single-use equipment.

Another possible solution could be to insert the UVC light source directly into the tube lumen. UVC Light emitting diodes (LEDs) are manufactured in different formats following industrial standards. The cross-sectional area of the active light emitting semiconductor chip is only a few square millimeters. But, in order to connect the diode to a power supply and protect the LED chip, the LED chip is typically incorporated into a larger package including, for example, a protective casing, a transparent window, a heat sink, etc. The overall size of the LED package is typically several millimeters in diameter. However, many medical devices such as endoscopes include channels having a typical diameter of 2-4 mm Therefore, it might be a challenge to insert the LED light source into the channel lumen of a medical device to be disinfected. Accordingly, the use of small diameter light delivery systems such as an optical fiber or a liquid light guide are required for the disinfection of medical devices having small diameter lumens.

Disinfection light emitted in a tube lumen filled with air is damped rapidly inside the tube lumen because the refractive index of air (1.00) is much lower than the refractive index of a typical tube wall made of polymer materials (e.g., 1.30-1.50). Disinfection efficiency could be improved substantially if the light rays were internally reflected during movement inside of the tube lumen. The preferred polymer tubing material used for endoscope channels is polytetrafluoroethylene (PTFE). This polymer has excellent mechanical properties and also unique optical properties. For example, if a high refractive index fluid is present in the PTFE endoscope channel, UVC light can propagate a substantial pathlength in the interior of the channel. If, however, the inner surface of the medical tubing is contaminated after many repeated recycles of use and cleaning by a thin layer of debris as found by Ofstead, the original favorable optical properties of novel PTFE tubes are unpredictable and likely degraded. The refractive index of these reused medical device channels is then expected to be higher than compared to new and unused ones.

Another possible tube material is a fluoropolymer, such as those manufactured by DuPont de Nemours, Inc., of Midland, Mich., and sold under the trademark TEFLON. One such fluoropolymer is fluorinated ethylene propylene (FEP), which has even better optical refractive properties than PTFE. It is possible to guide UVC light through very small diameter FEP tubing containing a high refractive index solution, such as a high concentration sodium chloride solution. The small diameter FEP liquid light guide fits into the PTFE endoscope channels and is easily moved through the PTFE tubing due to the excellent lubricities of the two materials described by their low static coefficient of friction.

Some embodiments of the present technology comprise a system and method for simultaneous cleaning and disinfection of the inner surfaces of narrow medical tubing such as catheters and endoscope channels. The system, when connected to the medical tubing, is configured to simultaneously (i) launch UVC light into the lumen of the medical tubing via a liquid light guide and (ii) flush the lumen with a flow of a sterile and transparent ionic solution to a distal end of the liquid light guide. The sterile ionic solution is provided from a reservoir connected to the light guide. The ionic solution flushes the tube lumen and provides, at the same time, the high refractive index fluid that enables liquid light guiding and maintains the disinfection capacity throughout the UVC treatment. Lumen parts with enclosures of opaque or absorbing fluid are flushed to a waste container through the open end of the medical tube. The continuous flush of UVC transparent ionic solution increases transparency in the medical tube lumen by removing debris that would otherwise absorb and scatter light. Endoscope channels, for instance, are mainly made of a low refractive index material such as PTFE fluoropolymer. The sterile ionic solution used to guide the UVC light in the liquid light guide and simultaneously flush the medical tube lumen can be an ionic solution with a relatively high refractive index compared to PTFE material. The high refractive index fluid increases the number of multiple inner reflections and consequently improves the disinfection efficiency compared to an air filled medical tube lumen.

In some applications, it is desired that the lumen of the medical device (e.g., the lumen of an endoscope) be kept dry. Accordingly, some embodiments of the present technology are configured to stop the flow of the sterile ionic solution before it exits the distal end of the light guide. In such embodiments, the light guide is still ready for light propagation, but no ionic solution is flushed into the lumen of the medical tube.

Some embodiments of the present technology provide a system and method for disinfecting and cleaning tube lumens and inner tube surfaces in diagnostic and therapeutic medical devices including all types of endoscopes. In certain embodiments, a system comprises a fluid reservoir with three connectors, a light source, a polymer tube configured to act as a liquid light guide and made of a low refractive index material (e.g., FEP or PTFE fluoropolymer), a sterile fluid reservoir, and a delivery mechanism configured to deliver a sterile ionic solution through the polymer tube. The light source can be in an axial position and in optical communication with the polymer tube (and a tube of a medical device to be disinfected) via a fluid chamber. Sterile high refractive index ionic solution from the fluid reservoir can flow into the fluid chamber from an off-axis position and further into the opening of the polymer tube. The liquid light guide can be moved back and forth inside a lumen of a medical device during disinfection treatment of the lumen. In some embodiments, the movement is done in a controlled manner with a motor driven system. A fluid consisting of organic residues, liquid residues from cleaning, and the sterile ionic solution exits a distal end of the medical tube and can be collected in a waste container for disposal.

In some embodiments, the fluid chamber is made as a connector with a sidearm of a disposable polymer material. The light source is connected in an axial position to the liquid light guide and the sterile ionic solution is delivered from the fluid reservoir through the sidearm of the connector and into the liquid light guide, thereby filling the light guide and, in certain embodiments, flushing the medical device lumen.

In some embodiments, the fluid chamber enables the liquid light guide to be in simultaneous communication with the light source and the fluid reservoir and the fluid chamber comprises a fluid-tight connector between the light source and the fluid reservoir. The fluid-tight connector can comprise a fluid-tight polymer window made of a UVC transparent polymer separating the UVC light source from the fluid. The fluid-tight polymer window can be transparent for UVC light and can be made of a fluoropolymer film or a cyclic olefin copolymer film.

In some embodiments, the liquid light guide (i.e., polymer tube) is prefilled with a high refractive index solution—such as a sterile ionic solution or an ethanol-water mixture that is transparent for UVC light. For example, the polymer tube can be filled with a saline solution (e.g., having a refractive index>1.34) and/or ethanol (ethyl alcohol; e.g., having a concentration that is >80% v/v and a refractive index>1.36). The liquid light guide can be made of FEP or PTFE fluoropolymer materials and can be closed in the distal end or in both ends. In such embodiments, no sterile fluid reservoir and connector part to a fluid reservoir are needed, and there is no flushing of the medical device lumen during UVC light exposure.

In some embodiments, the light source includes a housing having a light emitting diode (LED), focusing lens, power supply, electrical circuitry, cooling fans, an ultraviolet transparent window, and a connector part to mount to the fluid reservoir. In certain embodiments, the LED emits light in the range of 220-300 nm. In some embodiments, the light source is a visible light source (e.g., emitting light in the range of 400-700 nm) including a housing having a laser, lenses, electrical circuitry, a transparent window, and a connector part configured to be mounted on the fluid reservoir.

In some embodiments, the liquid light guide is in optical communication with the light source and configured to enable partly ultraviolet light transmission along its length such that the polymer tube has both a loss of light through part of its walls (e.g., along its length) and at the distal end.

In certain embodiments, the major loss of light occurs at the end of the liquid light guide. This can be accomplished by the use of high concentration ionic solution providing a high refractive index.

In some embodiments, the sterile ionic solution is a sodium chloride solution having, for example, a high solution concentration (e.g., >4%) and refractive index (e.g., >1.34).

In some embodiments, the medical device tubing can be made of low refractive index polymer materials such as PTFE and FEP. Accordingly, both the polymer tube and the medical device tube can be made of polymer materials having low static and kinetic coefficients of friction, thereby permitting the polymer tube to be able to slide into and move inside the medical device tube. For example, both the polymer tube and the medical device tube can be formed from fluoropolymer materials such as FEP and PTFE having a static coefficient of friction less than 0.1.

In some embodiments, the fluoropolymer tube has a proximal end having an expanded inner diameter such that the efficacy of launching the disinfection light into the small diameter fluoropolymer tubing is enhanced and loss of UVC light is minimized.

In some embodiments, a liquid light guide can be inserted into catheters—including urinary catheters, peritoneal catheters, and other catheters for delivery to blood vessels or body lumens—for the purpose of disinfecting the inner surfaces thereof. Thin (e.g., having a diameter smaller than or equal to 2 mm) fluoropolymer tubes filled with a saline solution are inserted into the catheter lumen guiding the disinfection light to the distal parts of the catheter. A steady flow of a saline solution through the liquid light guide during exposure with disinfection light flushes at the same time the inner lumen of the catheter before a lock solution is applied to the catheter. Flushing catheters with several milliliters of saline solution is a standard procedure. The liquid light guide then administers simultaneous disinfection and saline flushing. The light guide can include a connector part that can be used to close the catheter. A lock solution could be added to the catheter lumen via the port for saline flush. During the filling with a lock solution the disinfection light source is turned off. After the catheter is disinfected and filled, the fluid reservoir can be disconnected and disposed of.

In some embodiments, a liquid light guide can be inserted into supply lines for therapeutic fluids for disinfection and cleaning of the lumen of the supply lines. Therapeutic fluids comprise saline or saline-dextrose solutions and peritoneal dialysis fluids.

In some embodiments, a pump and suction system can be configured to both deliver a steady flow of a sterile liquid to the lumen of the liquid light guide and to empty the inner lumen of the medical device of liquid and fluid residues.

In some embodiments, the UV light source and inserted liquid light guide can run for prolonged periods in order to expose a medical device lumen with UVC light constantly for many hours. For example, the liquid light guide can be used for endoscopes during drying and storage to maintain sterility until repeated use. The present technology is expected to provide an increase in log reductions of pathogens throughout the full storage time of the endoscopes if UVC exposure is maintained. Further, in some embodiments, no hazardous chemical sterilants are needed if UVC exposure is applied after initial cleaning of the lumen.

II. SELECTED EMBODIMENTS OF SYSTEMS FOR DISINFECTING MEDICAL DEVICES

FIG. 1 is a partially schematic view of a system or assembly 10 for cleaning and disinfecting medical tubing (e.g., an endoscope) configured in accordance with an embodiment of the present technology. In the illustrated embodiment, the system 10 includes a fluid chamber 100, a UV light source 120, a tube (e.g., a polymer tube) configured to act as a liquid light guide 130 ("light guide 130"), and a fluid reservoir (e.g., a fluid source) 140 configured to supply a fluid 146. In some embodiments, the light guide 130 is manufactured from a fluoropolymer material such as PTFE or FEP fluoropolymers. In some embodiments, the fluid 146 is a transparent liquid with enhanced refractive index such as a sterile ionic solution (e.g., a high concentration sodium chloride solution). The fluid chamber 100 optically couples the UV light source 120 to the light guide 130 and fluidly couples the fluid reservoir 140 to the light guide 130.

The light guide 130 includes a lumen 132 that is open at both ends (i.e., at proximal and distal ends) and that enables the fluid 146 to propagate into and through the lumen 132. The light guide 130 is coupled to the fluid chamber 100 via a connector part 104 of the fluid chamber 100. The fluid 146 can be delivered into the light guide 130 via a pump system (not shown). Specifically, in the illustrated embodiment, the fluid 146 is delivered from the fluid reservoir 140 through a flexible tube 142 connected to a connector part 108 of an arm of 106 of the fluid chamber 100. The fluid 146 continues to flow into a proximal end (e.g., exit, opening, etc.) 116 of the light guide 130 and propagates inside the lumen 132 towards a distal end (e.g., exit, opening, etc.) 134 of the light guide 130.

The UV light source 120 is coupled to the fluid chamber 100 via a connector part 102. The light source 120 is separated from the ionic solution 146 in the fluid chamber 100 by a UV transparent polymer window 110. The connection between the UV light source 120 and the fluid chamber 100 is made watertight by a gasket, O-ring, or other similar structure (not shown). The UV light source 120 includes a UV light emitting diode (LED) 122 and a lens system (e.g., a front lens) 124 configured to focus the emitted UV light on/into the opening 116 of the light guide 130. In some embodiments, a window 128 is coupled to a distal portion of the UV light source 120. The window 128 separates the UV light source 120 from the fluid chamber 100, is in close proximity with the transparent polymer window 110, and is configured to protect the inner electrical and optical parts of the UV light source 120. In some embodiments, the window 128 is made from a transparent glass or quartz. In the illustrated embodiment, electrical wires 126 connect the UV light source 120 to an external electrical power source that enables longer operations of the cleaning and disinfection assembly 10. For shorter operations the UV light source 120 could run on electrical power from batteries.

In other embodiments, the fluid chamber 100 can comprise a three-way connector such as a Y-piece or a T-piece connector made of, for example, a fluoropolymer. In such embodiments, the three-way connector includes three connection ports for fluidly and optically coupling the UV light source 120 and the fluid reservoir 140 to the light guide 130. More specifically, in some embodiments, the first and second connection ports can be positioned in axially opposite positions, and a third connection port can be positioned at the end of a side arm. The fluid reservoir 140 can be mounted to the third one of the connection ports at the side arm of the three-way connector. A polymer window can be permanently mounted on the first axial port and close to the side arm, such that the first connection port is watertight. The light source 120 can be optically connected to the first (proximal) connection port. Lastly, the light guide 130 can be connected to/mounted on the second (distal) connection port.

The operation of the assembly 10 is now described in more detail. To clean or flush a medical tubing or tube 150 (e.g., a channel of an endoscope having a diameter of between about 2-8 mm) for residues, a constant flush of the fluid 146 can be applied. For example, in some embodiments, the light guide 130 can be inserted into and moved continuously in the forward/distal and/or reward/proximal directions inside the lumen of the medical tube 150. In some embodiments, the medical tube 150 has an open distal end 154. The flush with the liquid 146 (e.g., a sterile ionic solution) removes residues that are detached from the inner surface of the medical tube 150. During the flush, UV light propagates inside the light guide 130 and is launched (i) into the lumen of the medical tube 150 via the distal exit 134 of the light guide 130 and (ii) partly through the wall of the light guide 130. The UV light can disinfect the lumen of the medical tube 150 by killing microorganisms within the medical tube 150. In some embodiments, the UV light can be virucidal, fungicidal, etc.

The speed of movement of the light guide 130 inside the medical tube 150 can be varied in order to achieve a desired or required level of log reduction of the microorganisms (e.g., disinfection). In certain embodiments, the flow velocity of the fluid 146 from the reservoir 140 generated by the pump system does not directly impact the disinfection requirements. However, the continuous flow of the fluid 146 cleans the lumen of the medical tube 150 for detached debris and microorganisms. The concentration of the fluid 146, such as a sterile ionic solution, can be selected such that the fluid 146 enables a high transmittance of UV light in the light guide 130. In some embodiments, for example, the fluid 146 can be an inexpensive and non-toxic saline solution in high concentrations (e.g., from about 4-36%) that enables a high transmittance through the light guide 130, thereby maximizing the intensity of UV light exposed to the interior of the medical tube 150.

When the light guide 130 is made of low refractive index polymer, it is important that the lumen of the light guide 130 be free of contaminants that can absorb UVC light or stick to the inner surface which would result in an increase of the refractive index of the tube wall of the light guide 130. The foregoing effects can result in attenuation of the UV light propagation through the light guide 130, which can degrade the performance of the light guide 130. Accordingly, by flushing the light guide 130 with the fluid 146, the assembly 100 can provide constant UV light power throughout the light guide 130. In contrast, some conventional systems include a single tube for UV photochemical treatment of liquids. This means that the lumen of the light guide acts both as a reaction chamber and as a light guide. Photochemical treatment of a photo-active liquid means that the liquid to be treated necessarily absorbs UV light. As such, the liquid contains UVC-absorbing compounds in unknown concentrations. Furthermore, these compounds can potentially stick to the polymer wall resulting in an increase of the refractive index. Therefore, in such conventional systems, it is difficult to control the UV dosage applied to the various parts of the wall as the UVC light propagation is attenuated for the foregoing reasons. As described above, the present technology can deliver a controllable UVC dosage by flowing the fluid 146 through the light guide 130 and the medical tube 150.

Moreover, with a constant and steady flow of a pure high refractive index saline solution through the light guide 130, the openings of the light guide 130 and medical tube 150 remain open, unobstructed by organic debris or absorbing residual liquids. If the distal end 134 of the light guide 130 is closed by a plug or blocked by contaminants, UVC light can be inhibited or even prevented from propagating into and exposing the channel surface of the medical tube 150. By using, for example, a sterile and disposable fluoropolymer tube for the light guide 130, open at both ends, it is possible to control the UVC light exposure down the channel (e.g., the open distal end of the fluoropolymer tube will allow clearance of any potential organic debris in the channel by the steady flow of the high-refractive index saline solution).

The disinfection capability of the system 10 depends on, for example, the power of the UV light source 120, the transmittance of the fluid 146, the speed by which the light guide 130 is moved (e.g., translated) through the medical tube 150, the exposure time of the medical tube 150 to UV light from the UV light source 120, and the inner diameter of the medical tube 150, among other factors. When the light guide 130 is placed in the channel of the medical tube 150, it constantly emits light along its length to simultaneously expose all parts of the inner surface of the channel of the medical tube 150 to UV light.

The medical tube 150 to be cleaned and disinfected typically has a very narrow channel or lumen having a diameter down to few millimeters (e.g., less than about 10 mm, less than about 5 mm, less than about 3 mm, etc.). In order to insert and/or move the light guide 130 within the medical tube 150 when the medical tube 150 has a small inner diameter, the light guide 130 and the medical tube 150 both need to have a high degree of lubricity. Otherwise, the friction between the two tubes will inhibit or even prevent movement of the light guide 130 within the medical tube 150. Accordingly, in some embodiments, the medical tube 150 can be made from a fluoropolymer material such as PTFE. For example, endoscopes are typically made of a fluoropolymer material. Fluoropolymer materials have a high degree of lubricity and can therefore reduce the mutual friction between the medical tube 150 and the light guide 130. Specifically, PTFE and FEP fluoropolymers have very low coefficients of both static and dynamic friction (e.g., typically below 0.1) compared to other polymers such as silicone, polyvinylchloride (PVC) and polyurethane (PUR).

Therefore, by forming the light guide 130 from a fluoropolymer made of PTFE or FEP, the light guide 130 can move within the medical tube 150 even when the medical tube 130 has an inner diameter that is only slightly greater than an outer diameter of the light guide 130. Table 1 below illustrates representative outer diameters (OD) of the light guide 130 and inner diameters (ID) of the medical tube 150 for which tests were carried out. In each instance, the light guide 130 has an outer diameter that almost fits the inner diameter of the medical tube 150, and when tested, the light guide 130 was moved easily through an extended length of the medical tube 150 with the application of a gentle force.

TABLE 1

| Outer diameter (OD) second tube (light guide) | Inner diameter (ID) first tube (medical tube) |
|---|---|
| FEP (3.00 mm) | FEP (3.38 mm) |
| PTFE (3.09 mm) | FEP (3.38 mm) |
| FEP (2.75 mm) | PTFE (3.00 mm) |
| FEP (2.75 mm) | FEP (3.38 mm) |

More specifically, only a few tenths of a millimeter between the OD of the light guide 130 and the ID of the medical tube 150 is sufficient for an easy pull of the light guide 130 through a length of up to 1.4 m of the medical tube 150 when the tube materials are made of the above tested fluoropolymers. Additional tests verify that the above fluoropolymer tubes are easily pulled through the channels of used gastrointestinal endoscopes. In other tests (not shown), it has been demonstrated that the light from an LED with focusing optics can be launched into tube openings as small as 2 mm or smaller. Accordingly, in some embodiments, the proximal opening of the light guide 130 can have a diameter of 2 mm or smaller. As noted above, the diameter of the light guide 130 can at least be greater than 0.15 mm.

Some conventional systems describe inserting a light guide into a much shorter (e.g., compared to an endoscope) endotracheal tube with a substantially larger inner diameter than the diameter of the fluoropolymer tube which is closed at both ends (max ⅓ of the ID of the ET tubes). Therefore, there are no requirements for any of the tubes in such systems to be made of very lubricious materials. In contrast, the present technology includes both an endoscope channel and a light guide that are made of very lubricious materials, such as PTFE and FEP fluoropolymer. In this respect, these materials are outstanding compared to other polymers. Endoscope channels can be long (>1 m) and very narrow (down to 2 mm). At the same time, it is advantageous to maximize the diameter of the light guide in order to launch as much UVC light into the endoscope channel as possible. Therefore, the present technology advantageously enables a light guide having a diameter similar to that of an endoscope channel to move through the endoscope channel with minimal contact points as it is passed distally down the channel.

Figure 2:
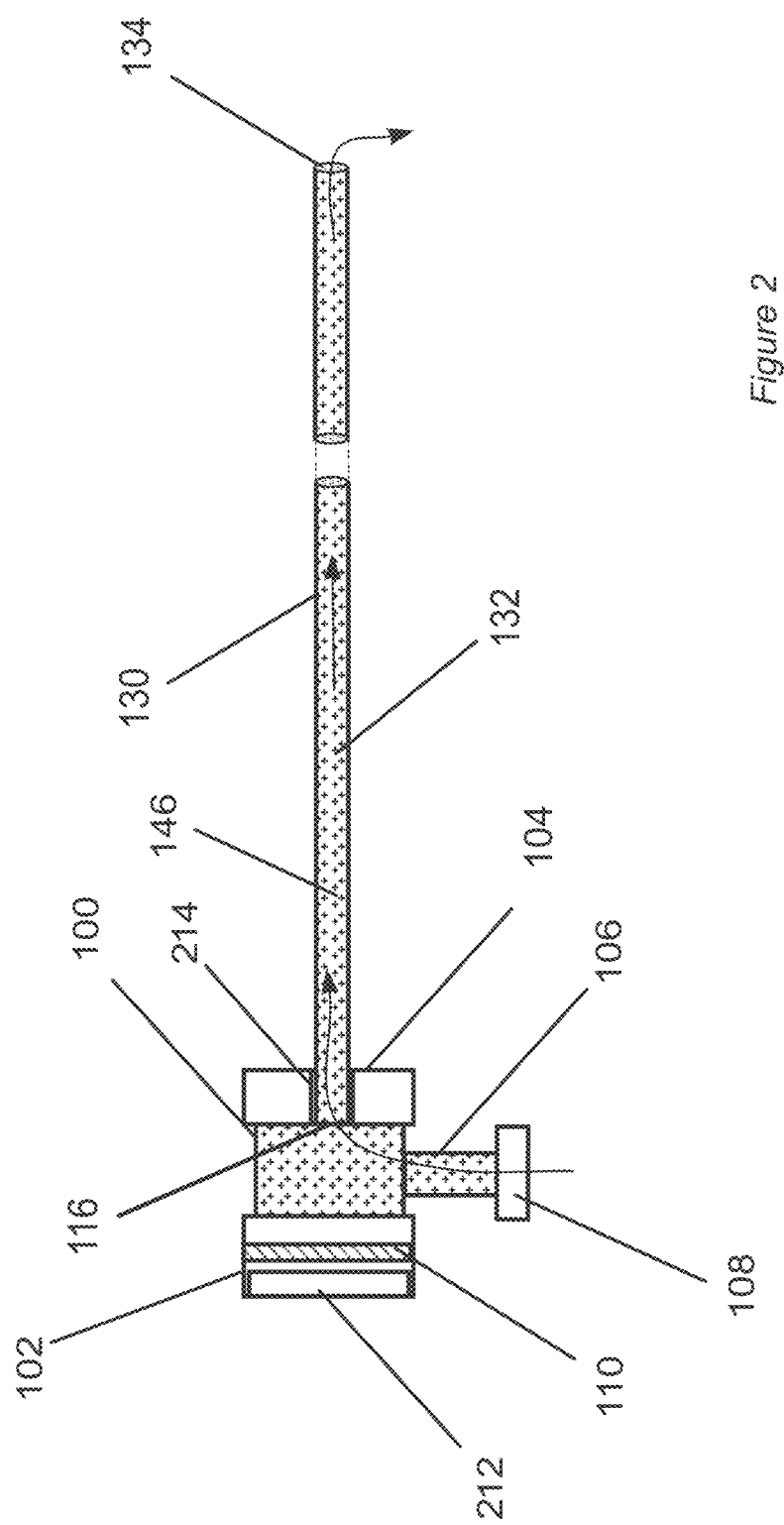
FIG. 2 is a partially schematic, enlarged, side view of a fluid chamber of the assembly shown in FIG. 1 configured in accordance with an embodiment of the present technology.

FIG. 2 is a partially schematic, enlarged, side view of the fluid chamber 100 showing flow of the fluid 146 in accordance with an embodiment of the present technology. The fluid 146 is injected from the fluid reservoir 140 (FIG. 1) through the flexible tube 142 (FIG. 1) to the arm 106 via the connector part 108 and into the fluid chamber 100. The fluid 146 enters the lumen of the light guide 130 through the proximal opening 116 and progresses to the distal end 134 where it exits the light guide 130 (e.g., into a waste bin and/or the medical tube 150). In the illustrated embodiment, the light guide 130 is placed in a hollow fixture 214 that includes a gasket or O-ring to keep the junction between the light guide 130 and the fluid chamber 100 substantially watertight. The light source 120 (FIG. 1) can be placed in a mount 212 configured to keep the light source 120 in a straight position and a fixed distance relative to the proximal opening 116 of the light guide 130.

Figure 3:
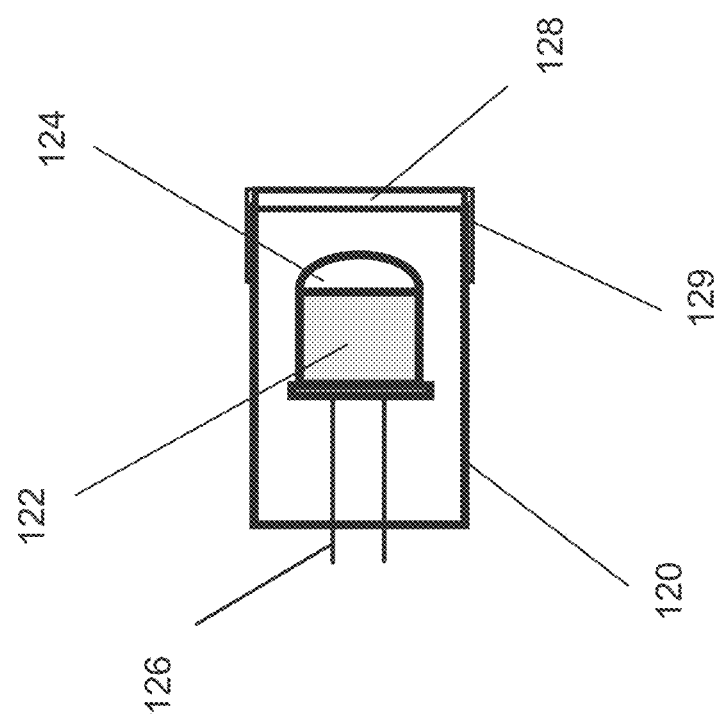
FIG. 3 is an enlarged side view of a light source of the assembly shown in FIG. 1 configured in accordance with an embodiment of the present technology.

FIG. 3 is an enlarged side view of the light source 120 configured in accordance with an embodiment of the present technology. The UV LED 122 is fixed on an electronic board (not shown). In some embodiments, the UV LED 122 emits light having a wavelength of between about 220-280 nm, which is germicidal and termed UVC light. The format of the UV LED 122 depends of the power emitted. For example, a high output power requires a high electrical current which can increase the level of heating of the LED housing. In the illustrated embodiment, the UV LED 122 is an example of a transistor outline package (TO package). In other embodiments, other package formats can be used. In certain embodiments, due to the relatively low UV light efficiency of the UV LED 122, the light source 120 includes a heat sink (not shown). The lens system 124 is configured to focus emitted UV light on/into the entrance (e.g., the proximal opening 116) of the light guide 130. The chosen lens system 124 depends on the format of the LEDs. In the illustrated embodiment, the lens system 124 is exemplified with a ball lens. The focal lens and spot size for a ball lens are typically a few millimeters. The window 128 can be a UV grade quartz window that protects the optics and electrical circuitry in case of leak of the fluid 146 (FIG. 1) through the polymer window. A connector part 129 fits into the mount 102 of the fluid chamber 100 (FIG. 1).

In some embodiments, the light source 120 is connected to a remote electrical power source via the electrical supply wires 126. In such embodiments, the light source 120 can be light-weight and easily mounted on (e.g., coupled to) the fluid chamber 100. The operation time for the disinfection of the medical tube 150 (FIG. 1; e.g., a one meter long endoscope channel) depends on a required level of disinfection. The electrical power consumption can therefore be substantial during a whole cleaning and disinfection cycle. In certain embodiments, a long treatment time excludes the use of rechargeable batteries. In other embodiments, the light source 120 can be powered by one or more batteries and/or other suitable sources of electrical power.

Figure 4:
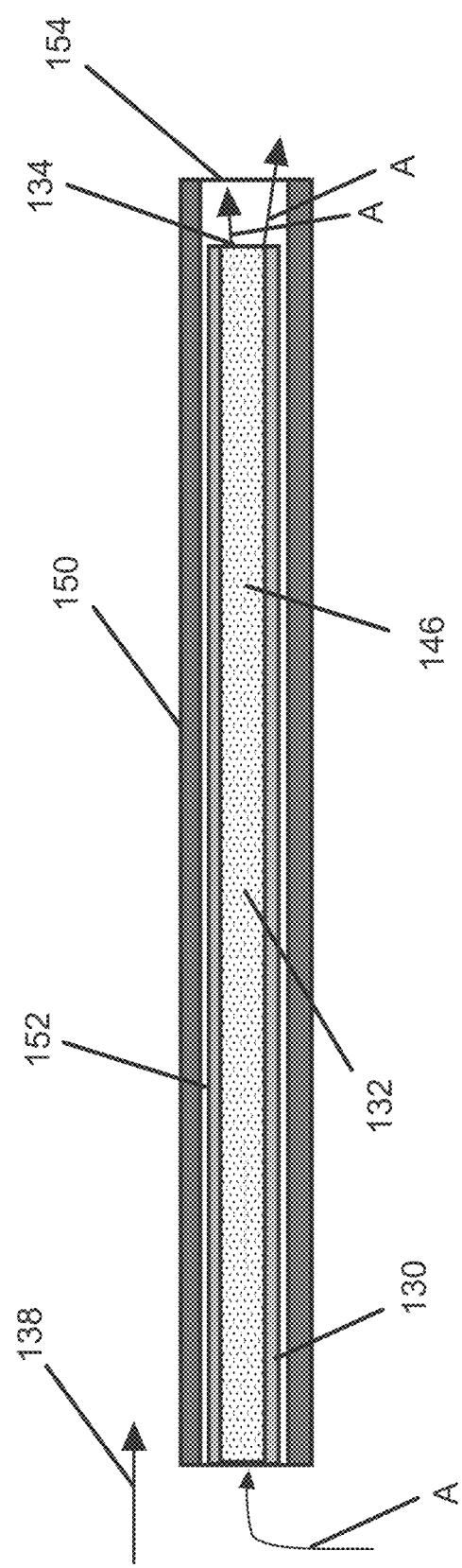
FIG. 4 is a partially schematic, enlarged, cross-sectional side view of a light guide of the system shown in FIG. 1 inserted into a medical tube in accordance with an embodiment of the present technology.

FIG. 4 is a partially schematic, enlarged, cross-sectional side view of the light guide 130 inserted into the medical tube 150 and being moved in a forward (distal) direction 138 in the lumen of the medical tube 150 in accordance with an embodiment of the present technology. In some embodiments, there is a small free space 152 between the walls of the light guide 130 and the medical tube 150. In other embodiments, the light guide 130 can have an outer diameter slightly smaller than, or substantially the same as, the inner diameter of the medical tube 150 such that there is substantially no free space 152 or a very small free space 152. As described in detail above, when both tubes are made of fluoropolymer materials, the friction is substantially minimized such that even very narrow medical tubing or channels can be penetrated by a tube with comparable diameter. In operation, the fluid 146 (e.g., an ionic solution such as a saline solution with a high concentration of sodium chloride and with an enhanced refractive index but still transparent in the UV spectral range) is injected into the lumen 132 of the light guide 130 and flushed through the light guide 130 to the distal end 134, as indicated by the arrows A. The fluid 146 flushes the interior of the medical tube 150 for potential debris and residual fluids before leaving the opening of the medical tube 150 at its distal end.

Figure 5:
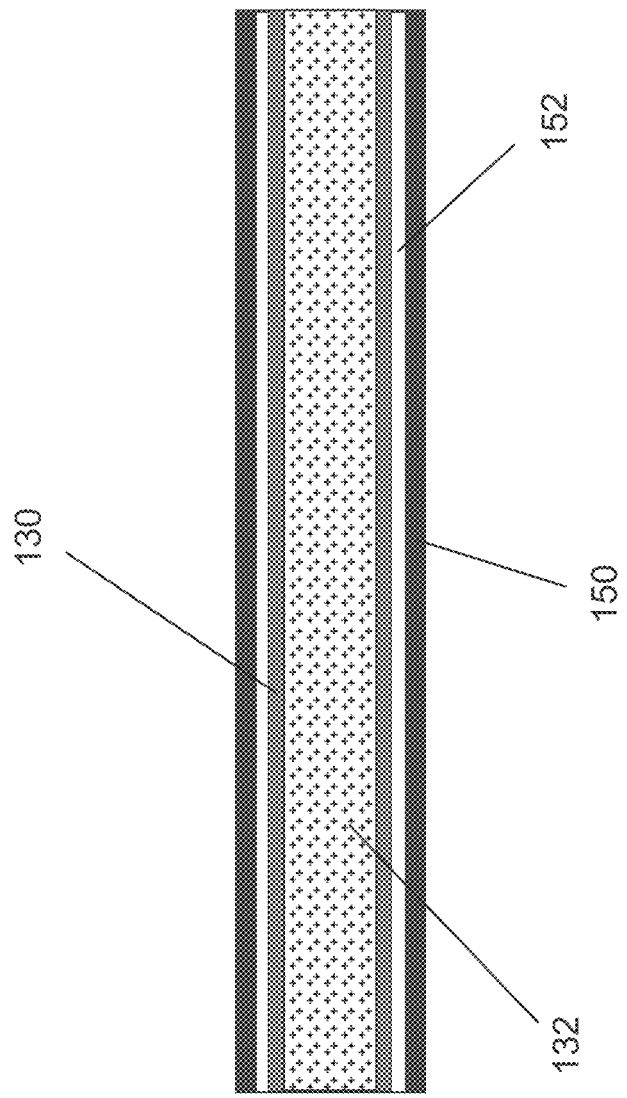
FIG. 5 is an enlarged, cross-sectional side view of the light guide and medical tube shown in FIG. 4.

FIG. 5 is an enlarged, cross-sectional side view of the light guide 130 inserted into the medical tube 150 and illustrating the optical properties of materials and fluid 146 in accordance with an embodiment of the present technology. In some embodiments, the light guide 130 is formed of a fluoropolymer such as FEP and/or PTFE. Both materials have low refractive indices compared to other polymers (e.g., having refractive indices down to about 1.30-1.35 [e.g., about 1.30-1.31] in the ultraviolet). The refractive index of PTFE, is normally slightly higher. In some embodiments, the fluid 146 can be a saturated ionic solution in a high concentration (e.g., NaCl and $MgCl_2$) that has a refractive index above about 1.36-1.40 in the visible spectral region. Literature suggests that the refractive indexes in the UVC spectral region can be even higher (e.g., about 1.40 for pure water). A saline solution with 25% wt. sodium chloride can reach a refractive index close to 1.38 in the visible spectral region.

Figure 6:
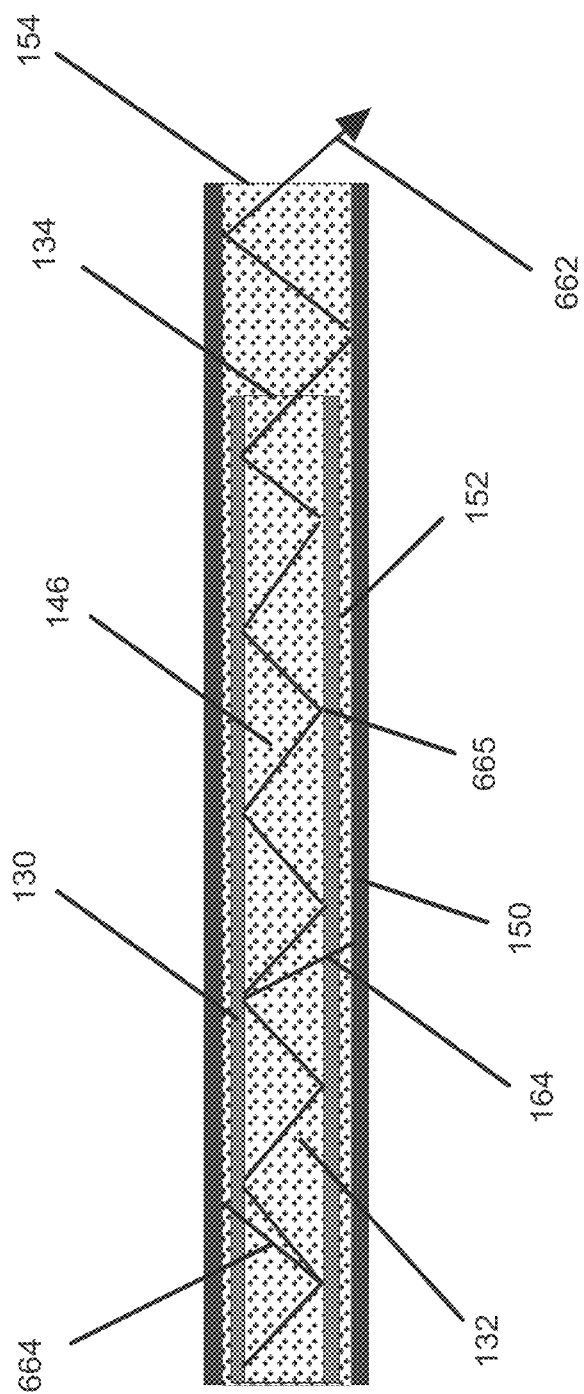
FIG. 6 is a partially schematic, enlarged, cross-sectional side view of the light guide and medical tube shown in FIG. 4 and showing propagation of UV light in accordance with an embodiment of the present technology.

FIG. 6 is a partially schematic, enlarged, cross-sectional side view of the light guide 130 inserted into the medical tube 150 and showing propagation of UV light 662 inside the light guide 130 in accordance with embodiments of the present technology. The fluid 146 is prepared in a high concentration such that its refractive index is higher than the fluoropolymer material of the wall of the light guide 130. Parts of the UV light 662 propagate inside the light guide 130 by internal reflections 665 due to the higher refractive index inside the light guide 130. At the same time, parts of the UV light 662 are lost by transmissions 664 through the wall along the length of the light guide 130. Both the fluid 146 and the transmitted light exit the open distal end 134 of the light guide 130 to simultaneously flush (via the fluid 146) and expose (via the UV light 662) the interior of the medical tube 150.

Referring to FIGS. 1-6 together, as noted above, the efficiency of the system 10 in disinfecting the medical tube 150 is dependent on, at least: the power of the UV light 662 launched into the light guide 130, the power of the UV light 662 on the inner surface of the channel of the medical tube 150, the concentration of the fluid 146, and the time the medical tube 150 is exposed to the UV light 662. Moreover, the length of the channel of the medical tube 150 (e.g., an endoscope channel) can be up to 1.2 m for selected types of endoscopes, and the length of the light guide 130 can exceed the length of the channel of the medical tube 150. Sometimes, the UV light 662 can be attenuated as it propagates to the distal exit 134 of the light guide 130. Therefore, the disinfection efficiency in the distal end 154 of the medical tube 150 (with a pre-set exposure time) can be reduced compared to the disinfection efficiency in the proximal end of the medical tube 150.

Accordingly, in some embodiments a second UV light source can be optically coupled to the distal exit 134 of the light guide 130 to increase the efficiency of disinfection near the distal end 154 of the medical tube 150. For example, a Y-piece connector, a T-piece connector, or a similar assembly as shown in FIG. 1 (e.g., including the fluid chamber 100, the UV light source 120, etc.) can be coupled to the distal end of the light guide 130 that extends past the distal end of the medical tube 150. A second UV light source can be mounted on an axial or other connection port of the Y-piece or T-piece connector, or to the connector part 102 (if a similar assembly as shown in FIG. 1 is mounted on the distal end of the light guide 130 exiting the channel of the medical tube 150). During operation, the fluid 146 can exit the light guide 130 via an off-axis or other port of the distal Y-piece or T-piece connector, the arm 106 of the assembly shown in FIG. 1, or another suitable port. If a Y-piece connector is used, the Y-piece connector can be configured with a UV transparent polymer window in an axial connection port thereof, which allows the second UV light source to be mounted thereto. Moreover, a liquid reservoir can be connected at a side arm of the Y-piece connector. Thus, in such embodiments both ends of the light guide 130 include a UV light source (e.g., a light source as shown in FIG. 3). In one aspect of the present technology, this can enhance the UV exposure of the inner surfaces of the channel of the medical tube 150. In another aspect of the present technology, the exposure and delivered germicidal dose of UV light is more evenly distributed along the channel of the medical tube 150.

Sometimes, debris can remain in the medical tube 150 after manual cleaning and high-level disinfection, prior to disinfection with the assembly 10. If a large amount of debris or a thick biofilm (collectively "bioburden") are present in the channel of the medical tube 150, part of this bioburden can attach to the surface of the light guide 130. The bioburden can absorb the UV light 662, thereby attenuating the UV light 662 transmitted through the light guide 130 and reducing the disinfection efficiency of the assembly 10. Accordingly, in some embodiments the assembly 10 can include a detector (e.g., a detector chip) configured to measure the power of the UV light 662 exiting the distal exit 134 of the light guide 130 to determine/confirm that the UV light 662 is launched correctly from the UV light source 120 into the light guide 130 and transmitted to the distal exit 134 of the light guide 130.

In some embodiments, two different UV power measurements can be carried out, each checking different potential performance issues. In the first UV power measurement, the detector collects all the UV light 662 that exits the distal exit 134 of the light guide 130. This measurement can check that a certain threshold power is obtained and that the UV light 662 is launched correctly into the light guide 130 from the light source 120. If the attenuation of the UV light 662 transmitted through the light guide 130 is below a set threshold, then the light guide 130 can be substituted with a new (e.g., disposable) light guide 130. In the second power measurement, the detector can be positioned on the side of the distal end of the light guide 130 on a part of the light guide 130 which is outside the channel of the medical tube 150 during use. The detector can therefore be in close contact with the surface of the light guide 130 and can measure the UV light 662 transmitted through the wall of the light guide 130. This measurement checks that a certain threshold power is transmitted through the wall of the light guide 130. A power level below the threshold could indicate that the light guide 130 has been coated with a thick biofilm when pulled through the channel of the medical tube 150. If the attenuation of the transmitted light through the wall of the light guide 130 is below a set threshold, then the light guide 130 can be substituted with a new (e.g., disposable) light guide 130. If threshold power of the UV light 662 is obtained, the disinfection procedure is initiated.

Figure 7:
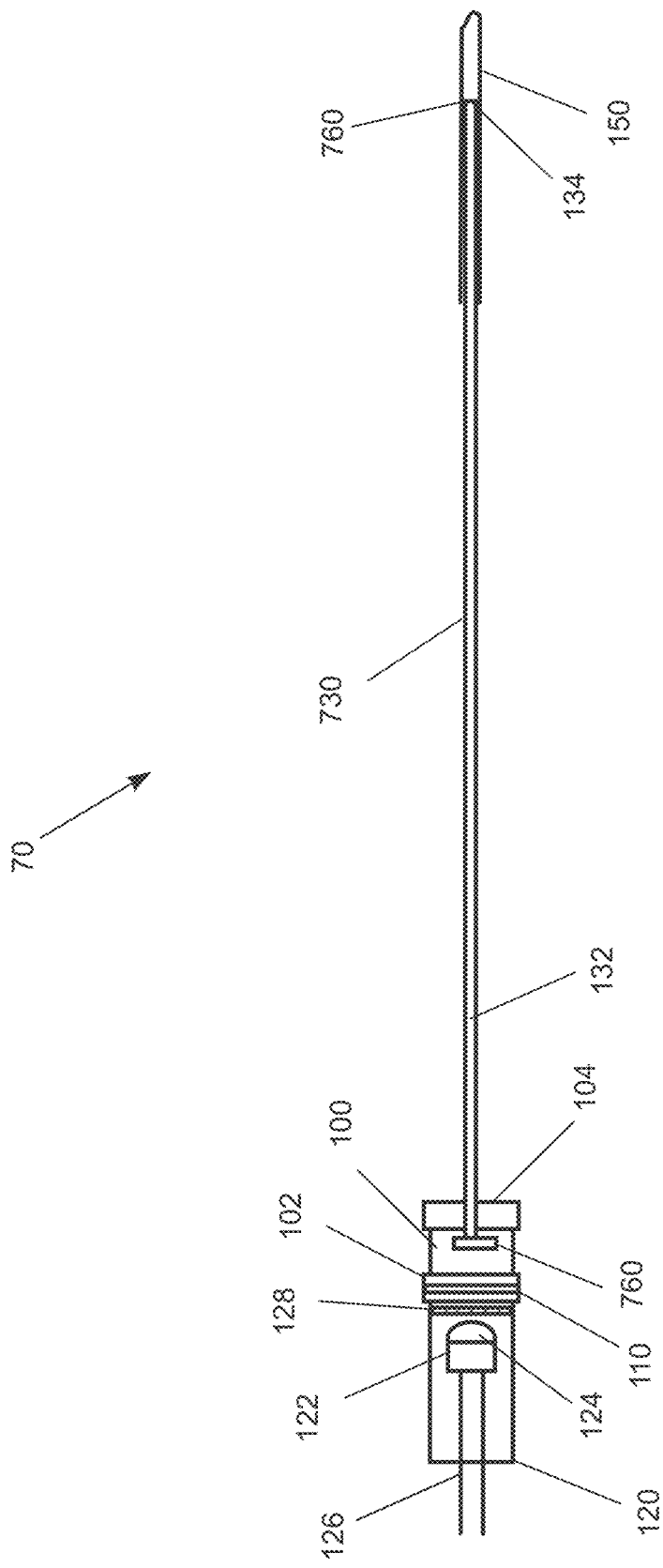
FIG. 7 is a partially schematic view of a system or assembly for cleaning and disinfecting medical tubing configured in accordance with another embodiment of the present technology.

FIG. 7 is a partially schematic view of a system or assembly 70 for cleaning and disinfecting medical tubing in accordance with another embodiment of the present technology. The assembly 70 can include some components generally similar to those described in detail above with reference to FIGS. 1-6. In the illustrated embodiment, however, the assembly 70 includes a light guide 730 that is (i) pre-filled with an ionic solution in a high concentration, and (ii) closed at both ends with transparent polymer films 760 in order to inhibit leakage of the ionic solution to the environment. In some embodiments, the polymer films 760 are made of fluoropolymer or COC polymer materials and have a transparency that enables UV light from the light source 120 both to be launched into the light guide 730 and emitted at the distal end 134 of the light guide 730 into the medical tube 150. During operation of the assembly 70 for a UV disinfection process, UV light is exposed partly from the distal end of the light guide 730 and along the wall of the light guide 730, and there is no flush of the interior space of the medical tube 150. The embodiment illustrated in FIG. 7 is simpler than the embodiment illustrated in FIG. 1, as no fluid reservoir and pump system are needed.

Figure 8:
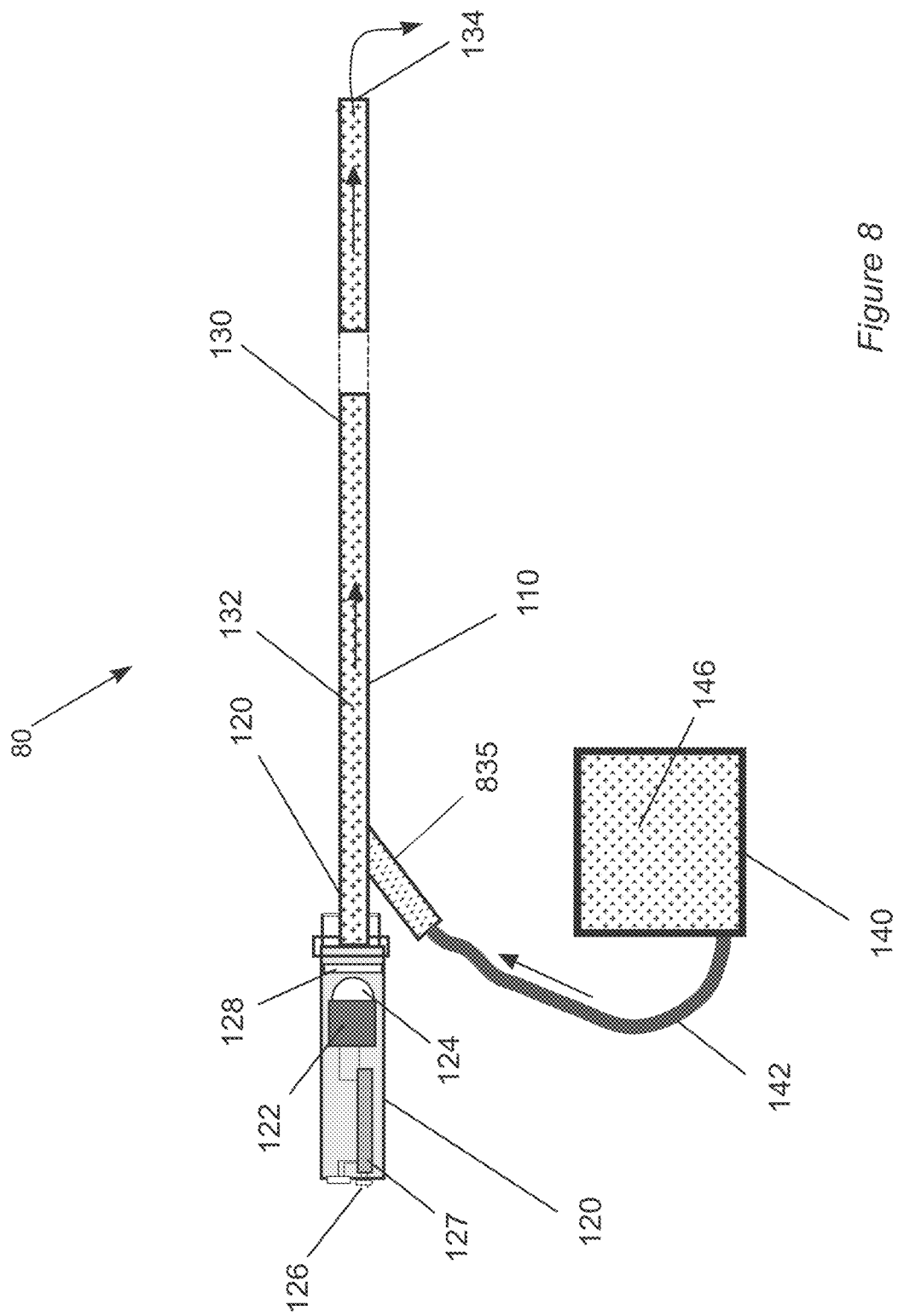
FIG. 8 is a partially schematic view of a system or assembly for cleaning and disinfecting medical tubing configured in accordance with another embodiment of the present technology.

FIG. 8 is a partially schematic view of a system or assembly 80 for cleaning and disinfecting medical tubing in accordance with another embodiment of the present technology. The assembly 80 can include some components generally similar to those described in detail above with reference to FIGS. 1-7. In the illustrated embodiment, however, the fluid reservoir 140 is connected directly to the liquid light guide 130 via a sidearm 835. The light source 120 is mounted in an axial position relative to the light guide 130 such that the light source 120, light guide 130, and fluid reservoir 140 form a Y-structure. The fluid reservoir 140 can deliver sterile ionic liquids, as well as ethanol-water mixtures, for flushing the lumen of the medical device tube 150 and/or for filling the light guide 130 with high refractive index liquids for enhanced light propagation. The light guide 130 can be open at the distal end for filling or flushing (FIG. 1) or it can be prefilled and then closed in both ends (FIG. 7).

Figure 9:
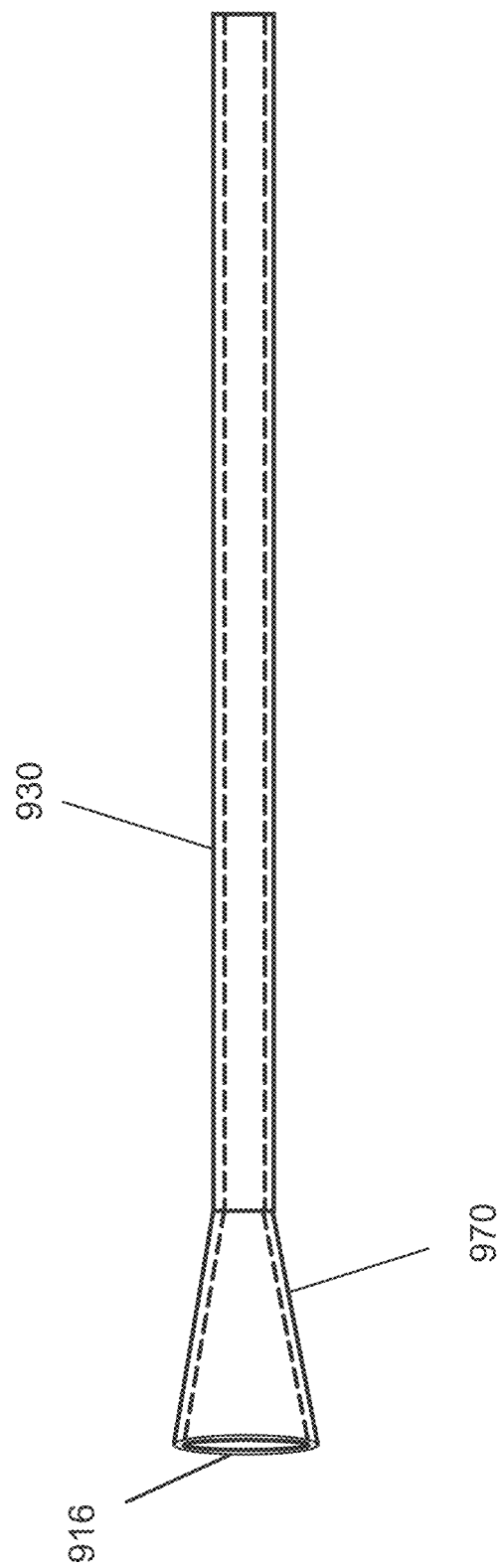
FIG. 9 is a partially schematic side view of a liquid light guide configured in accordance with an embodiment of the present technology.

FIG. 9 is a partially schematic side of a liquid light guide 930 configured in accordance with another embodiment of the present technology. In the illustrated embodiment, the light guide 930 has a tapered shape configured to facilitate transmission of the UV light into a lumen of the light guide 930. In some embodiments, even if the UV LEDs are equipped with focusing lenses (e.g., the lens system 124), a projected light spot (e.g., onto the proximal opening of a light guide) can still be several millimeters in diameter. However, in some embodiments, a light guide configured in accordance with the present technology can have a proximal opening with a small diameter of, for example, about 2-3 millimeters. Accordingly, the light guide 930 includes a tapered proximal portion 970 with an extended diameter at a proximal end or opening 916 that is configured to be positioned proximate to a UV light source (e.g., the UV light source 120). The illustrated embodiment can increase the input efficiency of the disinfection assembly. In some embodiments, the tapered portion 970 can be formed from the light guide 130 (FIG. 1) by expanding a proximal portion via thermoforming or another suitable method such that the liquid light guide 930 is still a single piece. In other embodiments, the light source 120 can alternatively or additionally include a tapered piece made of, for example, UV grade quartz. In other embodiments, the tapered portion 970 can be a separate part. For example, the tapered part 970 can be a molded connector part made from a fluoropolymer and the other part can be a thin fluoropolymer tube joined thereto.

Figure 10:
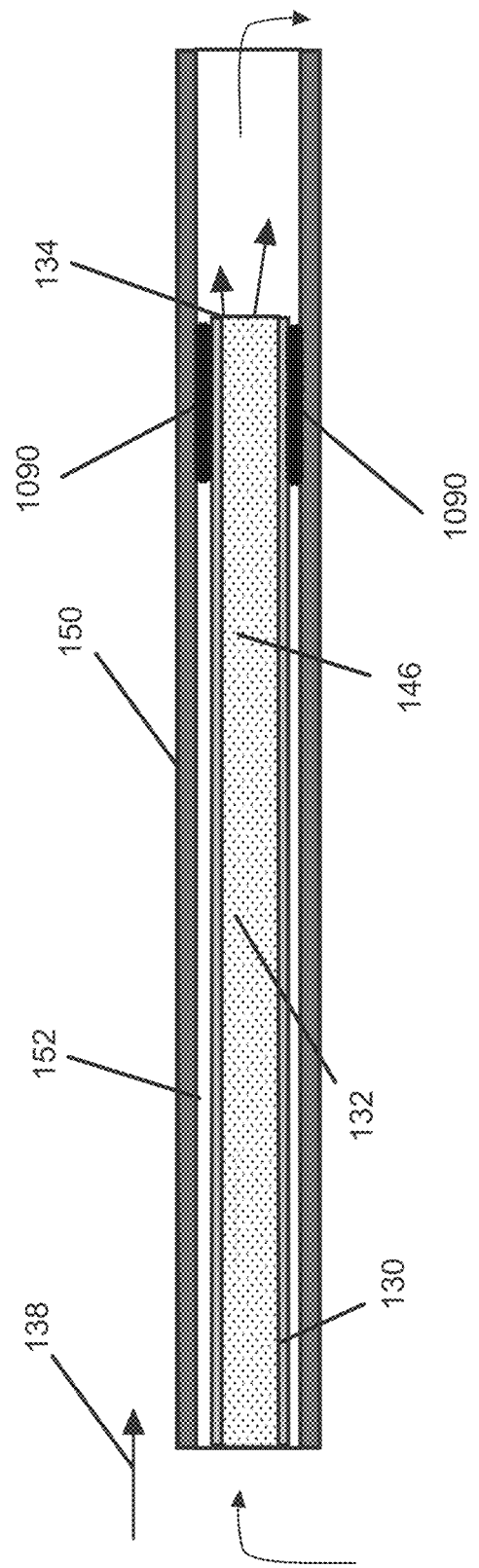
FIG. 10 is a partially schematic, enlarged, cross-sectional side view of a light guide of the assembly shown in FIG. 1 having a brush at its distal end in accordance with an embodiment of the present technology.

FIG. 10 is a partially schematic, enlarged, cross-sectional side view of the light guide 130 inserted into the medical tube 150 and having a brush 1090 at its distal end in accordance with an embodiment of the present technology. The brush 1090 can be a soft polymer brush configured to remove resides from the inner surface of the medical tube 150. Thus, the illustrated embodiment allows for a combined and simultaneous effect of brushing, flushing, and UVC light exposure of the medical tube 150 (e.g., an endoscope channel). The liquid light guide 130 with a brush 1090 can be (i) open in the distal end for a liquid flow or (ii) closed and filled with a sodium chloride solution. The channel walls of the medical tube 150 are irradiated both from UVC light which exits the distal end and through the thin wall material of the liquid light guide 130.

In other embodiments, the medical tube 150—rather than a separate tube—can be used as a light guide. As described above, the medical tube 150 is often made of PTFE fluoropolymers and/or other materials that conduct light if the lumen of the medical tube 150 is filled with a suitable fluid (e.g., a transparent and high refractive index ionic solution). Therefore, if the inner surface of the channel of the medical tube 150 is completely or substantially free of debris and bioburden, it has the potential to conduct light. Therefore, referring to FIG. 1, in some embodiments the UV light source 120 and the fluid reservoir 140 can be directly coupled to the channel of the medical tube 150 via, for example, a Y-piece connector, a T-piece connector, or an assembly generally similar to that of the assembly 10 shown in FIG. 1. In such embodiments, the channel of the medical tube 150 acts as the light guide 130. In some embodiments, a detector system (e.g., as described in detail above) can be used to monitor the output light power which exits the channel of the medical tube 150. If the measured light power exceeds a certain threshold value, then the disinfection procedure is initiated.

III. APPLICATION EXAMPLES: HIGH-LEVEL DISINFECTION OF ENDOSCOPE CHANNELS

After use of the endoscope, endoscopes are manually cleaning, followed by cleaning in automated washers. A liquid light guide, of any of the UV cleaning and disinfection assemblies described in detail above, can then be inserted into the endoscope channels for disinfection prior to placing the endoscope in a safety cabinet for drying before it is used again. In particular, the present technology allows the endoscope channel to be flushed with a sterile ionic solution (e.g. a high concentration saline solution) in order to remove residues and enhance UV light propagation in the channel during UV light irradiation. In other embodiments, the light guide is a closed light guide with no flush of an ionic solution. In both cases, the light guide can be moved inside the channel to its end. During movement of the liquid light guide, UV exposure takes place from the distal end and through the wall of the light guide. In certain embodiments, during storage, the light guide is maintained in the lumen of the entire length of the endoscope channel such that the channel is constantly exposed to UV light over a prolonged time period. Contrary to conventional systems that use sterilants, the present technology enables constant UV exposure and thus disinfection until the endoscope is to be used again. Accordingly, the present technology can advantageously (i) increase the log reduction of pathogens (e.g., roughly one log reduction for doubling the exposure time), and (ii) keep the endoscope high-level disinfected throughout its storage.

When the endoscope if flushed with an ionic solution (e.g., the embodiment illustrated in FIG. 1), the endoscope can be flushed with ethanol or sterile water to remove salt before long-term UV exposure is initiated with the liquid light guide placed in the endoscope channel during storage. In other embodiments, the flush can be done with an alcohol-water mixture through the liquid light guide in order to clean the endoscope channel of residues before UV light exposure. After flushing the endoscope channel, the liquid light guide will be introduced into the lumen filled with the light-enhancing ionic chloride solution. Surface tension in the small diameter light guide tubing ensures that the ionic solution is maintained in the tube lumen during use. When the light guide is in place, UV exposure of the channel can be applied during endoscope storage.

In some embodiments, the fluid reservoir can first be filled with a saline solution and then exchanged with (i) a reservoir containing alcohol for disinfection/drying of the endoscope channel, (ii) a reservoir of heated air for drying the endoscope channel, and/or (iii) a pump configured to provide negative pressure (e.g., suction) for removing residual liquid from the endoscope channel.

In sum, different embodiments of the present technology for cleaning and disinfection with UV light can include, for example:
  1. The UV technology is used after the automatic washing procedure. The channel is flushed with a saline solution which both flushes the channel for debris and also acts as light propagating liquid. After the pre-set UV exposure time, the endoscope channel is flushed with ethanol and placed in a storage cabinet.

2. The UV technology is used as above, and in addition, UV exposure is maintained after ethanol flush and during endoscope storage. When applied in this configuration, the liquid light guide can be either a closed tube with a high concentration saline solution or an open-ended light guide filled with the saline solution. In both cases, the UV exposure can be done simultaneously and in the entire length of the endoscope lumen.

3. The endoscope is cleaned manually and then placed in an automated endoscope washer followed by an ethanol flush as per usual reprocessing protocol. Then, the UV technology with a closed liquid light guide can be placed in the endoscope channel during storage in the safety cabinet.

As set forth above, endoscopes have a working channel through which different tools can be guided to the distal end of the endoscope and exit the distal end for manipulation in a patient—such as visual inspection, management of bleeding sites, biopsy sampling, etc. Often, a mechanical structure called an elevator arm is present in the distal end of duodenoscopes. The elevator arm, and its position, is controlled by a wire in a closed channel of the duodenoscope. Optical and mechanical parts at the distal end of the duodenoscope, including the elevator arm and a working channel, may become contaminated with debris and microorganisms during use in a patient. This occurs because the distal end of the duodenoscope is in direct contact with the mucosal surface of the gastrointestinal tract. The length of the working channel may become contaminated when biopsies are removed and drawn backwards to the proximal end of the duodenoscope. A suction channel of the duodenoscope can become contaminated when fluid is drawn up from the distal end of the duodenoscope.

Accordingly, a liquid light guide of any of the UV cleaning and disinfection assemblies described in detail above, can be used in each channel after manual cleaning and high-level disinfection. This can be done before storage of the duodenoscope and/or during storage of the endoscope. More specifically, the light guide extends through the duodenoscope and beyond the distal end of the duodenoscope such that the light guide exposes the entire length of the working channel with UV light. If the duodenoscope has an elevator arm, then the UV light guide can be placed in close contact with the proximal portion of the elevator arm if the elevator arm is placed in a horizontal position. The side of the elevator arm in close contact with the light guide is then exposed to UV light simultaneously with the inner surface of the duodenoscope channel.

IV. EXAMPLES

The following examples are illustrative of several embodiments of the present technology:

1. A system for disinfecting a medical device, the system comprising:
   a liquid light guide including an elongated tube defining a lumen, wherein the elongated tube has a distal end portion defining a distal opening of the lumen, and wherein at least the distal end portion is configured to be slidably positioned within a lumen of the medical device;
   a fluid reservoir fluidly coupled to the elongated tube and configured to deliver a fluid at least partially through the lumen of the elongated tube to the distal opening; and
   a UV light source optically coupled to the lumen of the elongated tube, wherein the elongated tube has a refractive index that is less than a refractive index of the fluid such that light from the light source propagates distally through the lumen of the elongated tube toward the distal opening.

2. The system of example 1 wherein the elongated tube is formed from a polymer.

3. The system of example 1 or example 2 wherein the elongated tube has an outer diameter, and wherein the lumen of the medical device has an inner diameter that is larger than the outer diameter of the elongated tube by less than about 0.5 millimeters.

4. The system of any one of examples 1-3 wherein the elongated tube has an outer diameter, and wherein the lumen of the medical device has an inner diameter that is larger than the outer diameter of the elongated tube by less than about 0.25 millimeters.

5. The system of any one of examples 1-4 wherein the elongated tube has an outer diameter, and wherein the lumen of the medical device has an inner diameter that is about equal to the outer diameter of the elongated tube.

6. The system of any one of examples 1-5, further comprising a fluid chamber, wherein—
   the fluid reservoir is fluidly coupled to the fluid chamber,
   the elongated tube includes a proximal end portion coupled to the fluid chamber and defining a proximal opening of the lumen of the elongated tube, and
   the UV light source is coupled to the fluid chamber and configured to direct light into the proximal opening of the lumen of the elongated tube.

7. The assembly of example 6 wherein the fluid chamber is formed as a 'Y' or 'T' piece connector part with three openings and the fluid is delivered directly from the fluid source into the elongated tube.

8. The system of example 6 or 7, further comprising a transparent polymer window positioned between the light source and the fluid chamber.

9. The system of any one of examples 1-8, wherein—
   the elongated tube includes a proximal end portion defining a proximal opening of the lumen of the elongated tube,
   the UV light source is positioned to direct light into the proximal opening of the elongated tube, and
   the fluid reservoir is fluidly coupled to the proximal opening of the elongated tube via a fluid chamber or a connector part having three openings.

10. The system of any one of examples 1-9 wherein the elongated tube is made of a fluoropolymer material, wherein the medical device is made of the fluoropolymer material, and wherein a coefficient of friction between the elongated tube and medical device is less than about 0.1.

11. The system of any one of examples 1-10 wherein the fluid is a sterile saline solution.

12. A method for disinfecting a lumen of a medical device, the method comprising:
   positioning at least a portion of an elongated tube of a liquid light guide within the lumen of the medical device;
   flowing a fluid into the elongated tube such that the fluid flows (a) at least partially through a lumen of the elongated tube and (b) from a distal opening of the elongated tube into the lumen of the medical device, wherein the fluid has a refractive index that is greater than a refractive index of the elongated tube; and while flowing the fluid, directing UV light into the elongated tube such that the UV light propagates (a) distally along the lumen and (b) from the distal opening into the lumen of the medical device.

13. The method of example 12, further comprising moving the elongated tube distally and/or proximally within the lumen of the medical device while flowing the fluid.

14. The method of example 12 or 13 wherein the fluid is a high concentration UV transparent sodium chloride solution having a refractive index that is greater than or equal to 1.34, ad wherein the elongated tube is made from a fluoropolymer material having a refractive index that is less than or equal to 1.34.

15. The method of any one of examples 12-14 wherein the fluid is a saline solution, and wherein the method further comprises, after flowing the saline solution, flowing ethanol and/or sterile water into the elongated tube such that the ethanol and/or sterile water flows (a) at least partially through the lumen of the elongated tube and (b) from the distal opening of the elongated tube into the lumen of the medical device.

16. A system for disinfecting a lumen of an endoscope, the system comprising:
a fluid chamber;
a liquid light guide including an elongated tube having a proximal opening fluidly coupled to the fluid chamber and a distal opening, wherein at least a portion of the elongated tube is configured to be slidably positioned within the lumen of the endoscope, and wherein the portion of the elongated tube has an outer diameter that is less than about 0.5 millimeters smaller than an inner diameter of the lumen of the endoscope;
a fluid source coupled to the fluid chamber, wherein the fluid source is configured to deliver a fluid through the elongated tube and from the distal opening of the elongated tube; and
a UV light source configured to direct UV light into the proximal opening of the elongated tube, wherein the fluid has a refractive index that is greater than a refractive index of the elongated tube so that the UV light propagates through the elongated tube and from the distal opening.

17. The system of example 16 wherein the UV light source is configured to emit UV light having a wavelength of between 220 to 300 nm, wherein the UV light source is axially aligned with the proximal opening of the elongated tube, and further comprising focusing optics configured to focus the UV light into the proximal opening of the elongated tube.

18. The system of example 17, further comprising a transparent optical window coupled to the fluid chamber, wherein the optical window separates the UV light source from the fluid in the fluid chamber.

19. The system of any one of examples 16-18 wherein the elongated tube is made of a fluoropolymer material, wherein the endoscope is made of a fluoropolymer material, and wherein a coefficient of friction between an outer surface of the elongated tube and an inner surface of the endoscope is less than about 0.1.

20. The system of any one of examples 16-19 wherein the fluid is a saline solution having a concentration that is larger than 4%.

21. An assembly for disinfection of tube lumens, the assembly comprising:

a first polymer tube with a narrow lumen to be disinfected in a material with a low coefficient of friction;
a second partly UV transparent polymer tube open in both ends and with a diameter smaller than the first polymer tube and a with a comparable low coefficient of friction as the first polymer tube, which allows the second polymer tube to slide inside the narrow lumen of the first polymer tube and with a refractive index, $N_P$, the second polymer tube is filled with a ionic solution with refractive index, $N_L$, delivered from a fluid reservoir and where $N_L>N_P$, which allows fluid and light to propagate simultaneously in the second polymer tube and irradiate the lumen of first polymer tube;
a UV light source in optical communication with the second polymer tube; and
a fluid reservoir enabling fluid flow and light propagation comprising a first connector port joined to the light source, and a second connector port joined to the second polymer tube, the light source is in axial position to and in optical communication with the second polymer tube via the fluid chamber, the first connector port is fluid-tight and separates the light source from the fluid passing the fluid chamber with a transparent polymer window, and a third connector port open to the fluid chamber and in communication with the fluid reservoir,
wherein light from the light source and liquid from the fluid reservoir propagates via the fluid reservoir and into the proximal end of the first polymer tube through the lumen and to the distal end of the first polymer tube, the first polymer tube is then inserted into the opening of and moved to the distal end of the second polymer tube simultaneously exposing with light and flushing with a liquid fluid the inner lumen of the second polymer tube, waste fluid is collected at the exit of the second tube.

22. The assembly of example 21 wherein the light source is a light emitting diode emitting ultraviolet light ranging from 220 to 300 nm.

23. The assembly of example 22 wherein the ultraviolet light emitting diode emits a total power larger than 5 mW.

24. The assembly of any one of examples 21-23 wherein the first polymer tube has a refractive index $N_P$ less than 1.34.

The assembly of any one of examples 21-24 wherein the first polymer tube has an outer diameter less than 3 mm.

26. The assembly of any one of examples 21-25 wherein the first polymer tube is made of fluoropolymer material.

27. The assembly of any one of examples 21-26 wherein the second polymer tube is made of fluoropolymer material.

28. The assembly of example 27 wherein the concentration of the saline solution is larger than 4%.

29. The assembly of any one of examples 21-28 wherein the liquid fluid is a sterile saline solution.

30. The assembly of any one of examples 21-29 wherein the refractive index of the fluid, $N_F$, is larger than the refractive index of the first polymer tube, $N_F>N_P$.

31. The assembly of any one of examples 21-30 wherein the fluid reservoir continuously delivers a fluid flow.

32. The assembly of any one of examples 21-31 wherein the static coefficient of the first and second polymer tubes are <0.1.

33. An assembly for cleaning and disinfecting endoscope channels, the assembly comprising:
an ultraviolet C light source with focusing optics and an optical window;

a first fluoropolymer tube open in both ends and with refractive index $N_P$ less than 1.34 and diameter less than 3 mm;

an endoscope channel accessible in both ends and with an inner diameter larger than the outer diameter of first polymer tube;

a fluid reservoir configured to contain a saline solution; and a fluid reservoir comprising a first connector port joined to the light source, and a second connector port joined to the first fluoropolymer tube, the light source is in an axial position to and in optical communication with the first fluoropolymer tube via the fluid reservoir, the first connector port is fluid-tight and separates the light source from the fluid reservoir with a transparent polymer window, and a third connector port open to the fluid reservoir and in communication with the fluid reservoir, wherein ultraviolet light from the light source and a saline solution from the fluid reservoir is configured to propagate, via the fluid reservoir, into the lumen of the first fluoropolymer tube when the first fluoropolymer tube is inserted into the opening of, and moved to the distal end of, the endoscope channel thereby simultaneously exposing and flushing with light and liquid fluid the inner lumen of the endoscope channel.

34. The assembly of example 33 wherein the endoscope channel is made of a fluoropolymer material.

35. The assembly of example 33 or 34 wherein the refractive index of the fluid, $N_F$, is larger than the refractive index of the first polymer tube, $N_F > N_P$.

36. The assembly of any one of examples 33-35 wherein the light emitting diode emits a total power larger than 5 mW.

37. The assembly of any one of examples 33-36 wherein the concentration of the saline solution is larger than 4%.

38. The assembly of any one of examples 33-37 wherein the polymer window is made of a cyclic olefin copolymer.

39. The assembly of any one of examples 33-38 wherein the first polymer tube is tapered to an opening larger than 3 mm in its proximal end.

40. A method for disinfecting endoscopic channels, the method comprising:

mounting a disinfection assembly to an endoscope channel to be exposed with UV light, wherein the assembly comprises a polymer tube in communication with a light source mounted on a first connector port of a fluid reservoir, wherein the polymer tube is composed of a low refractive index fluoropolymer material with a refractive index less than or equal to 1.34;

filling the polymer tube, via the reservoir, with a UV transparent sodium chloride solution having a refractive index $N_F$ greater or equal to 1.34 when filled, inserting and moving the polymer tube through an endoscope channel lumen and exposing inner surfaces of the endoscope channel to light, wherein the polymer tube is moved from a proximal end of the endoscope channel lumen toward a distal end of the endoscope channel lumen and then retracted, wherein during UV light exposure, a flow rate of the UV solution is controlled and can be chosen to be a steady flow, wherein the UV solution flushes the endoscope channel and is collected as waste at an exit portion of the endoscope channel.

41. A system for disinfecting a lumen of a catheter, the system comprising:

a fluid chamber;

a liquid light guide including an elongated tube having a proximal opening fluidly coupled to the fluid chamber and a distal opening, wherein at least a portion of the elongated tube is configured to be moveable positioned within parts of the catheter lumen, and wherein the portion of the elongated tube has an outer diameter that is less than the inner diameter of the lumen of the catheter;

a fluid source coupled to the fluid chamber, wherein the fluid source is configured to deliver a fluid through the elongated tube and from the distal opening of the elongated tube; and a UV light source configured to direct UV light into the proximal opening of the elongated tube, wherein the fluid has a refractive index that is greater than a refractive index of the elongated tube so that the UV light propagates through the elongated tube and from the distal opening.

42. The system of example 41 wherein the catheter is made of polymer with a refractive index greater than 1.40.

43. The system of example 41 or 42 wherein the fluid chamber is formed as a 'Y' or 'T' piece connector part with three openings and the fluid is delivered directly from the fluid source and into the elongated tube.

V. CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. Moreover, the various embodiments described herein may also be combined to provide further embodiments. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms may also include the plural or singular term, respectively. Additionally, the term "comprising" is used throughout to mean including at least the recited feature(s) such that any greater number of the same feature and/or additional types of other features are not precluded. Directional terms, such as "upper," "lower," "front," "back," "vertical," and "horizontal," may be used herein to express and clarify the relationship between various elements. It should be understood that such terms do not denote absolute orientation. Further, while advantages associated with certain embodiments of the technology have been described in the context of those embodiments, other embodiments may also exhibit such advantages, and not all embodiments need necessarily exhibit such advantages to fall within the scope of the technology. Accordingly, the

We claim:

1. An assembly for disinfection of tube lumens, comprising:
   a first polymer tube with a narrow lumen to be disinfected in a material with a low coefficient of friction;
   a second partly UV transparent polymer tube open in both ends and with a diameter smaller than the first polymer tube and a with a comparable low coefficient of friction as the first polymer tube which allows the second polymer tube to slide inside the narrow lumen of the first polymer tube and with a refractive index, $N_P$, the second polymer tube is filled with a ionic solution with refractive index, $N_L$, delivered from a fluid reservoir and where $N_L > N_P$, which allows fluid and light to propagate simultaneously in the second polymer tube and irradiate the lumen of first polymer tube;
   a UV light source in optical communication with the second polymer tube; and
   a fluid chamber enabling fluid flow and light propagation comprising a first connector port joined to the light source, and a second connector port joined to the second polymer tube, the light source is in axial position to, and in optical communication with, the second polymer tube via the fluid chamber, the first connector port is fluid-tight and separates the light source from the fluid passing the fluid chamber with a transparent polymer window, and a third connector port open to the fluid chamber and in communication with the fluid reservoir;
   wherein light from the light source and liquid from the fluid reservoir propagates via the fluid chamber and into the proximal end of the first polymer tube through the lumen and to the distal end of the first polymer tube, the first polymer tube is then inserted into the opening of and moved to the distal end of the second polymer tube simultaneously exposing with light and flushing with a liquid fluid the inner lumen of the second polymer tube, waste fluid is collected at the exit of the second tube.

2. The assembly of claim 1 wherein the light source is a light-emitting diode emitting ultraviolet light ranging from 220 to 300 nm.

3. The assembly of claim 2 wherein the ultraviolet light-emitting diode emits a total power larger than 5 mW.

4. The assembly of claim 1 wherein the first polymer tube has a refractive index $N_P$ less than 1.34.

5. The assembly of claim 1 wherein the first polymer tube has an outer diameter less than 3 mm.

6. The assembly of claim 1 wherein the first polymer tube and/or the second polymer tube are composed of fluoropolymer material.

7. The assembly of claim 1 wherein the liquid fluid is a sterile saline solution.

8. The assembly of claim 1 wherein the refractive index of the fluid $N_F$ is larger than the refractive index of the first polymer tube $N_P$.

9. The assembly of claim 1 wherein the fluid reservoir continuously delivers a fluid flow.

10. The assembly of claim 1 wherein the static coefficient of the first and second polymer tubes are <0.1.

11. An assembly for cleaning and disinfecting endoscope channels, the assembly comprising:
    an ultraviolet C light source with focusing optics and an optical window;
    a first fluoropolymer tube open in both ends and with refractive index $N_P$ less than 1.34 and diameter less than 3 mm;
    an endoscope channel accessible in both ends and with an inner diameter larger than the outer diameter of first polymer tube;
    a fluid reservoir configured to contain a saline solution; and
    a fluid chamber comprising a first connector port joined to the light source, and a second connector port joined to the first fluoropolymer tube, the light source is in an axial position to and in optical communication with the first fluoropolymer tube via the fluid chamber, the first connector port is fluid-tight and separates the light source from the fluid chamber with a transparent polymer window, and a third connector port open to the fluid reservoir and in communication with the fluid chamber,
    wherein ultraviolet light from the light source and the saline solution from the fluid reservoir is configured to propagate, via the fluid chamber, into a lumen of the first fluoropolymer tube when the first fluoropolymer tube is inserted into an opening of and moved to a distal end of the endoscope channel thereby simultaneously exposing and flushing with light and liquid fluid an inner lumen of the endoscope channel.

12. The assembly of claim 11 wherein the endoscope channel is made of a fluoropolymer material.

13. The assembly of claim 11 wherein the refractive index of the fluid $N_F$ is larger than the refractive index of the first polymer tube $N_P$.

14. The assembly of claim 11 wherein the light emitting diode emits a total power larger than 5 mW.

15. The assembly of claim 11 wherein the polymer window is made of a cyclic olefin copolymer.

16. The assembly of claim 11 wherein the first polymer tube is tapered to an opening larger than 3 mm in its proximal end.

17. A method for disinfecting endoscopic channels, the method comprising:
    mounting a disinfection assembly to an endoscope channel to be exposed with UV light, wherein the assembly comprises a polymer tube in communication with a light source mounted on a first connector port of a fluid reservoir, wherein the polymer tube is composed of a low refractive index fluoropolymer material with a refractive index less than or equal to 1.34;
    filling the polymer tube, via the reservoir, with a UV transparent sodium chloride solution having a refractive index $N_F$ greater or equal to 1.34; and
    when filled, inserting and moving the polymer tube through an endoscope channel lumen and exposing inner surfaces of the endoscope channel to light, wherein the polymer tube is moved from a proximal end of the endoscope channel lumen toward a distal end of the endoscope channel lumen and then retracted,
    wherein during UV light exposure, a flow rate of the UV solution is controlled and can be chosen to be a steady flow,
    wherein the UV solution flushes the endoscope channel and is collected as waste at an exit portion of the endoscope channel.

* * * * *